United States Patent
Fernando et al.

(10) Patent No.: US 6,727,480 B2
(45) Date of Patent: Apr. 27, 2004

(54) WATERLESS VESSEL HEATING SYSTEM AND METHOD

(75) Inventors: C. J. Anthony Fernando, Durham, NC (US); James E. Swon, Chapel Hill, NC (US); Michael F. Haw, Raleigh, NC (US)

(73) Assignee: Varian, Inc., Palo Alto, CA (US)

( * ) Notice: Subject to any disclaimer, the term of this patent is extended or adjusted under 35 U.S.C. 154(b) by 331 days.

(21) Appl. No.: 09/911,103

(22) Filed: Jul. 23, 2001

(65) Prior Publication Data

US 2002/0014485 A1 Feb. 7, 2002

Related U.S. Application Data

(63) Continuation-in-part of application No. 09/603,305, filed on Jun. 23, 2000, now Pat. No. 6,303,909.

(51) Int. Cl.⁷ .............................. H05B 3/36; G01N 1/38
(52) U.S. Cl. ...................... 219/549; 219/429; 219/528; 73/866
(58) Field of Search ................................. 219/385, 386, 219/429, 436, 528, 549; 366/143; 422/68.1, 82.12; 73/866

(56) References Cited

U.S. PATENT DOCUMENTS

| | | |
|---|---|---|
| 3,092,704 A | 6/1963 | DeWoody et al. |
| 3,299,253 A | 1/1967 | Lawson, Jr. |
| 3,584,198 A * | 6/1971 | Doi et al. ................... 219/528 |
| 3,791,221 A | 2/1974 | Kirschner et al. |
| 3,791,222 A | 2/1974 | Goodlart et al. |
| 3,877,817 A | 4/1975 | Ralston |
| 3,935,726 A | 2/1976 | Heinz |
| 4,149,066 A | 4/1979 | Niibe |

(List continued on next page.)

FOREIGN PATENT DOCUMENTS

| | | |
|---|---|---|
| GB | 757616 | 9/1956 |
| WO | 92/10294 | 6/1992 |
| WO | 95/23329 | 8/1995 |

OTHER PUBLICATIONS

Minso Thermal–Clear Transparent Heaters & Heater/Sensors, Mar. 29, 2000, pp. 1–4.*
Minco, Inc., "Thermofoil (TM) Heaters & Controllers", http://www.minco.com, Jun. 9, 1999.
U.S. Pharmacopeia, "USP 23–NF 18", 19th ed., pp. 4660–4669, Nov. 15, 1998.
Brinker et al., "Bathless Dissolution: Validation of System Performance", Dissolution Technologies, pp. 7–14, May 22, 1998.

*Primary Examiner*—Joseph Pelham
(74) *Attorney, Agent, or Firm*—David Gloekler; Bella Fishman

(57) ABSTRACT

A dissolution testing system comprises a vessel plate on which a plurality of vessels are mounted. Each vessel includes a lateral wall having an outer surface around which a plurality of flexible heater elements are attached. Each heater element includes a transparent surface area, a heat conductive element extending along the transparent surface area, a temperature sensing element extending along the transparent surface area, and an electrical contact element connected to the heat conductive element and the temperature sensing element. The heater element can have more than one heating zone, with at least one of the heating zones being selectively energizable. The transparent heater element allows unobstructed view into the interior of its vessel, and reduces the time required to achieve a stabilized set point temperature in the vessel. A heater control system communicates with each heat conductive element and each temperature sensing element through a corresponding one of the electrical contact elements. The heater control system permits each vessel to be controlled independently of the other vessels.

50 Claims, 12 Drawing Sheets

U.S. PATENT DOCUMENTS

| | | | | |
|---|---|---|---|---|
| 4,412,125 A | * | 10/1983 | Nagasawa et al. | 219/549 |
| 4,466,276 A | | 8/1984 | Ruyak et al. | |
| 4,754,657 A | | 7/1988 | Schneider | |
| 4,777,351 A | * | 10/1988 | Batliwalla et al. | 219/528 |
| 4,797,537 A | | 1/1989 | Berthelius et al. | |
| 4,858,155 A | | 8/1989 | Okawa et al. | |
| 4,879,917 A | | 11/1989 | Eppelmann et al. | |
| 4,952,783 A | * | 8/1990 | Aufderheide et al. | 219/528 |
| 5,589,649 A | | 12/1996 | Brinker et al. | |
| 5,682,001 A | * | 10/1997 | Hanson et al. | 73/866 |
| 6,170,980 B1 | | 1/2001 | Martin | |
| 6,174,497 B1 | | 1/2001 | Roinestad et al. | |
| 6,423,948 B1 | * | 7/2002 | Kwasnoski et al. | 219/385 |

* cited by examiner

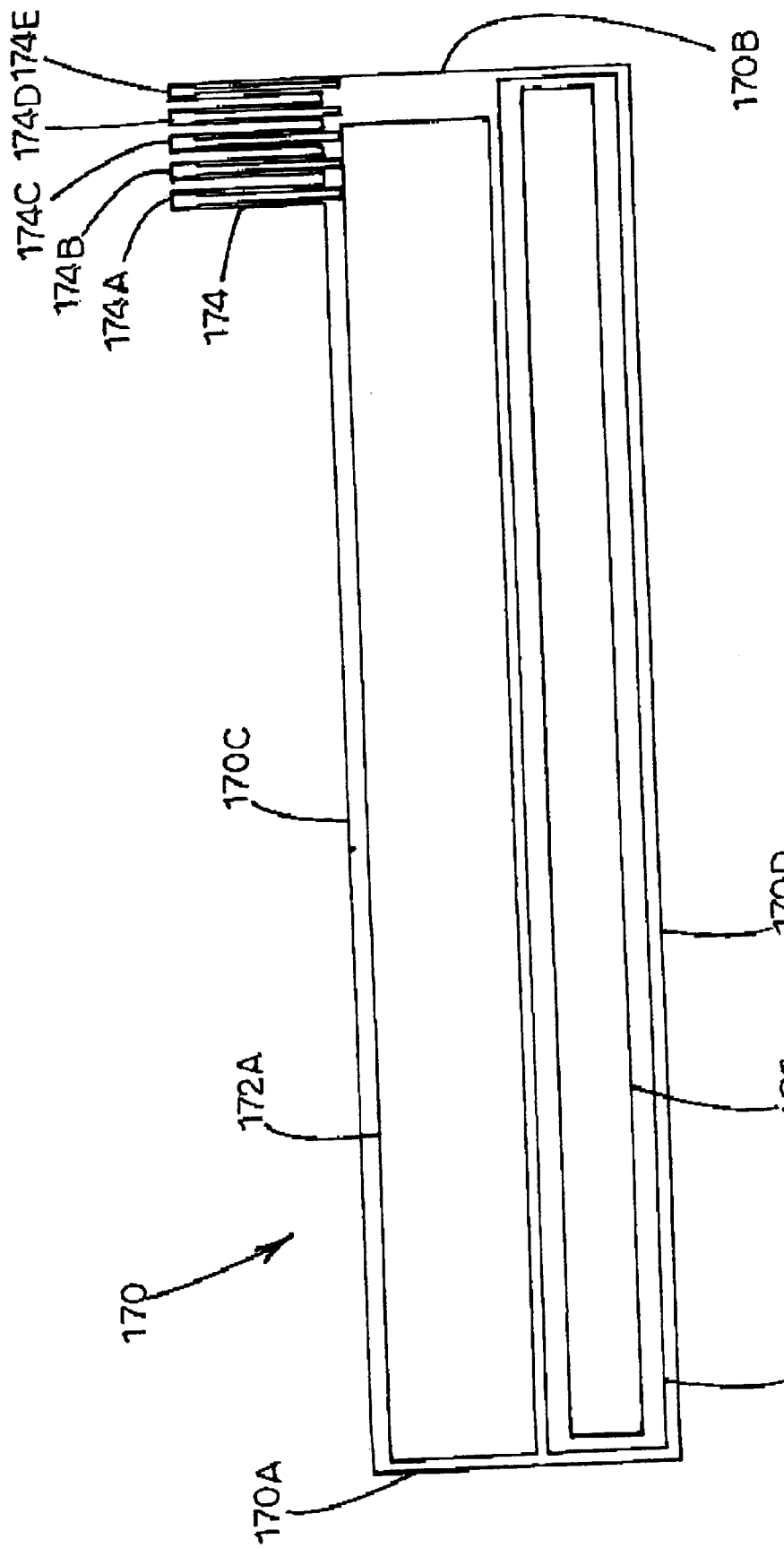

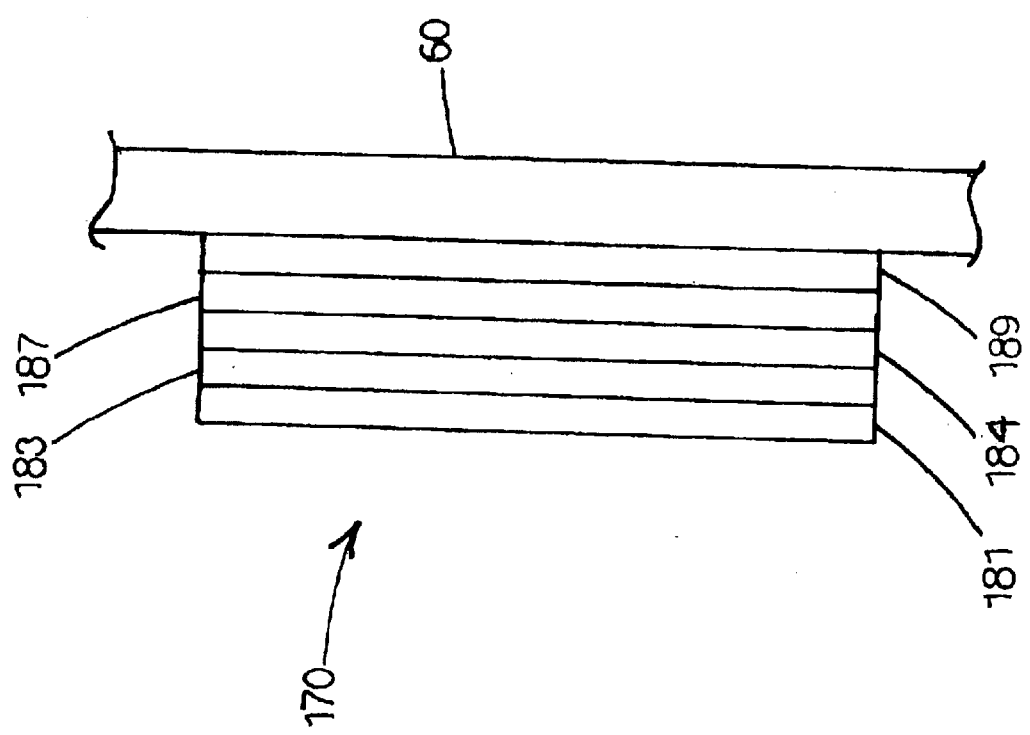

WATERLESS VESSEL HEATING SYSTEM AND METHOD

This is a continuation in part of application Ser. No. 09/603,305, filed Jun. 23, 2000, now U.S. Pat. No. 6,303,909.

TECHNICAL FIELD

The present invention relates to the preparation or testing of heated sample media contained in vessels and, more particularly, to the controlled heating of sample media in the vessels without the use of a water bath.

BACKGROUND ART

In the pharmaceutical industry, the controlled heating of sample media in vessels is an important step in sample preparation procedures. Examples of such procedures include those performed for the purpose of testing and analyzing the rate at which dosages release from pharmaceutical products such as tablets, filled capsules or transdermal patches. The dosages are released in solutions under controlled conditions which may or may not be representative of the human digestive process, contact with the skin, or implantation within the body. The procedural steps, test duration, dissolution medium, and apparatus employed in any given dissolution test must comply with United States Pharmacopeia (USP) guidelines in order for the test to be accepted as valid for the specific dosage or delivery system tested.

For instance, the general requirements of Section 711 (Dissolution) of USP 23-NF18, Ninth Supplement, Nov. 15, 1998, specify a particular apparatus, termed "Apparatus 1," which includes a covered vessel made of plastic, glass or other inert, transparent material that does not absorb, react, or interfere with the specimen being tested; a motor; a metallic drive shaft; and a cylindrical basket. Other devices may be specified from time to time for stirring, mixing or retaining the delivery system during the test procedure.

The vessel may be cylindrical with a hemispherical or flat bottom and sides which are flanged at the top. The dimensions of the vessel are specified according to the nominal volumetric capacity of the vessel. A fitted cover can be used to retard evaporation from the vessel and, when used, must provide sufficient openings to allow the ready insertion of a thermometer and withdrawal of specimens. Also included are requirements for the dimensions, construction material, position in relation to the vessel, and performance of the shaft and other operative components. Importantly, the vessel must be either partially immersed in a water bath of placed in a heating jacket to hold the temperature inside the vessel at 37±0.5° C. or other specified temperature. When using a water bath, the bath fluid must be kept in constant, smooth motion.

FIG. 1 illustrates a conventional dissolution testing apparatus generally designated 10. Apparatus 10 includes a main housing or head 12 containing a programmable systems control module. Head 12 is situated above a vessel plate 14 and a water bath container 16, and is typically motor-driven for vertical movement toward and away from vessel plate 14. Peripheral elements located on head 12 include an LCD display 18 for providing menus, status and other information; a keypad 21 for providing user-inputted operation and control of spindle speed, temperature, test start time, test duration and the like; and readouts 23 for displaying information such as RPM, temperature, elapsed run time, or the like. Water must be heated and circulated through water bath container 16 by means such as external heater and pump modules (not shown), which may be combined into a single heater/circulator module. Water bath container 16 thus requires a fluid transfer means such as tubing 25, as well as a drain line 27 and valve 29.

Vessel plate 14 supports a plurality of vessels 31 extending into the interior of water bath container 16. Typically, three, four, six or eight vessels 31 can be supported. Each vessel 31 has a standard shape characterized by a lateral cylindrical section 31A, a bottom hemispherical (or flat) section 31B, and a flanged section 31C around the mouth of vessel 31. Vessels 31 are locked and centered in place on vessel plate 14 by means such as ring lock devices or clamps (not shown). A stirring element including a motor-driven spindle 37A and paddle 37B operates in each vessel 31. Individual clutches 39 can be provided to alternately engage and disengage power to each spindle 37A. A dosage delivery module 41 is used to preload and drop dosage units (e.g., tablets) into each vessel 31 at prescribed times and bath (or vessel) temperatures. An automated sampling manifold 45 lowers and raises sampling cannulae 47 into and out of each respective vessel 31. Sampling manifold 45 can also be vertically movable between head 12 and vessel plate 14. Sampling cannulae 47 operate in conjunction with a bidirectional peristaltic pump (not shown), and are used during the dissolution testing procedure to periodically withdraw samples from the vessel media for analysis. Samples could also be taken manually using pipettes and/or sampling cannula/syringe assemblies. Miniature temperature probes 49 associated with each vessel 31 can also be located on sampling manifold 45.

In a typical operation, dosage units are dropped into the bottoms of each solution-containing vessel 31 and each paddle 37B rotates at a predetermined rate and duration within the test solution as the dosage units dissolve. In other types of tests, a cylindrical basket (not shown) loaded with a dosage unit is substituted for each paddle 37B and rotates within the test solution. For any given vessel 31, the temperature of the test solution must be maintained at a prescribed temperature (e.g., 37° C.). Solution temperature is maintained by immersion of vessel 31 in the water bath of water bath container 16. Accordingly, the temperature of the test solution is dependent upon, and thus indirectly controlled by, the temperature of the water bath which in turn is dictated by the external heating means employed. Temperature probe 49 is used to monitor the test solution temperature, and can be any suitable type of transducer such as a thermistor.

As recognized by those skilled in the art, the use of a water bath in connection with an apparatus such as dissolution testing apparatus 10 has some drawbacks. First, water bath container 16 is necessarily large in order to accommodate the immersion of several vessels 31, and hence requires a significant volume of water to serve as the medium for transferring heat energy to the media or solution contained in vessels 31. Consequently, an undue amount of time and energy is required to initially dispense the volume of heated water into water bath container 16 and bring each vessel 31 to the desired set point temperature. The volume of water also adds to the overall weight of apparatus 10. Second, an external heater and water circulation system is required. It might be possible to eliminate the water circulation system by providing an external resistive heating plate or coil to heat the water bath. Such a resistive heating element, however, would necessarily be quite large in order to heat the entire volume of the water bath, require a large amount of electrical energy to operate, and would not appreciably reduce the amount of startup time required to bring vessels 31 to a desired set point temperature. Third, the water bath system does not allow for individualized control of each vessel 31. The ability to control the heating profile of a given vessel 31 or group of vessels 31 independently and distinct from other vessels 31 of dissolution testing apparatus 10 would be quite useful during many types of procedures. Fourth, biological growth, scaling, and other impurities tend to collect in the water bath, such that the use of the water bath entails cleaning maintenance and the addition of preservatives or additives, all of which adds to the cost of the water bath system.

One approach to eliminating the need for a water bath and controlling the temperatures of individual vessels, while still conforming to USP dissolution requirements, is disclosed in U.S. Pat. No. 5,589,649 to Brinker et al. The embodiments disclosed therein provide individual flexible, resistive heater elements attached to and wrapped around the lateral cylindrical section of the outside wall of each vessel. Each heater element is divided into horizontally-oriented upper and lower heating areas having differing power ratings (e.g., 100W, 200W, etc.). The heating areas are controlled by the associated dissolution testing apparatus through lead wires. Lead wires are provided separately for each heating area and are connected directly to the controller section of the apparatus. Accordingly, each heater element taught by Brinker et al. in effect contains two heating devices or elements. Each heater element is required to be held in place on its vessel by a spring-loaded stainless steel jacket. The jacket is profiled to provide a gap between the jacket and the heater element. Because the vessel is not immersed in a heat-providing water bath, a reflective coating is attached to the hemispherical section of the vessel in order to reduce heat loss from the vessel and reduce the time required to bring the test solution to the desired solution temperature.

The temperature control system disclosed in Brinker et al. requires the use of a modified stirring element for each vessel. The shaft of the modified stirring element is hollow. A temperature sensor such as a resistive thermal device (RTD), thermocouple or thermistor is located near the bottom of the hollow interior of the stirring element shaft in physical thermal contact therewith, and generates signals representative of temperature measured within the vessel. Power to this temperature sensor and the signals generated thereby are transmitted through a cable running through the hollow length of the stirring element shaft, through a signal transfer device located at the top of the shaft, and through a second cable connected to the control circuitry of the dissolution testing apparatus.

The requisite jacket is disadvantageous in that it impairs or, in some cases, almost completely obstructs a view of the contents of the vessel and the stirring element operating therein. This problem is especially critical in view of the fact that USP Section 711 expressly indicates that the dissolution apparatus should preferably permit observation of the specimens and stirring element during testing. Moreover, the jacket does not completely insulate the vessel from external thermal influences such as room air conditioning, heating, ventilation, and open doors. In addition, the customized stirring element and its requisite electrical components, as well as the need for the addition of a reflective coating, are believed to be unduly complex and expensive solutions to the problems presented by current vessel heating systems.

Accordingly, there remains a need for a more practical, effective, and energy efficient solution to providing a vessel heating system that does not require a water bath and that can independently control individual vessels in a vessel-containing system such as a dissolution testing apparatus. The present invention is provided to address these and other problems associated with vessel heating systems.

DISCLOSURE OF THE INVENTION

According to one aspect of the present invention, a heater element comprises a plurality of clear, flexible films, a temperature sensing element, and a heat conductive element. The temperature sensing element is interposed between the films, and includes an elongate temperature sensing portion extending over a surface area of the heater element along a first alternating, serpentine course. The heat conductive element is also interposed between the films, and includes an elongate heat conductive portion extending over the surface area of the heater element along a second alternating, serpentine course adjacent to the first course. An electrical contact element is connected to the heat conductive element and the temperature sensing element.

In one embodiment, the heater element includes an internal adhesive. The temperature sensing element is adhered to a first side of the internal adhesive, and the heat conductive element is adhered to a second side of the internal adhesive.

In another embodiment, the heater element includes three films. The temperature sensing element is interposed between the first and second films, and the heat conductive element is interposed between the second and third films.

In yet another embodiment, the heater element comprises a plurality of films, including a first film and a second film. The temperature sensing and heat conductive elements are interposed between the first film and the second film.

In a further embodiment, the heater element comprises a first heating zone and a second heating zone. The heat conductive element has at least one portion running through the first heating zone, and at least one other portion running through the second heating zone. A common electrical contact interconnects the first and second heating zones. In use, depending on the level of liquid to be heated in a vessel to which the heater element is attached, either one or both heating zones is energized to provide dissipative heat. Preferably, the temperature sensing element extends through only one of the heating zones, e.g., the heating zone that operates regardless of liquid level.

According to another aspect of the present invention, a heater element comprises a plurality of clear, flexible films, a temperature sensing element, a heat conductive element, and an electrical contact element connected to the heat conductive element and the temperature sensing element. The temperature sensing element and the heat conductive element are each interposed between the films. The temperature sensing element includes an elongate temperature sensing portion, which extends over a surface area of the heater element and defines an embedded wire pattern.

According to yet another aspect of the present invention, a vessel heating system comprises a vessel and a flexible heater element. The vessel includes a lateral wall having an outer surface to which the heater element is attached. The heater element includes a transparent surface area, a heat conductive element extending along the transparent surface area, a temperature sensing element extending along the transparent surface area, and an electrical contact element connected to the heat conductive element and the temperature sensing element.

In one embodiment, the heater element is adhered to the vessel using a pressure-sensitive adhesive.

In another embodiment, the heater element is baked directly onto the vessel using a suitable adhesive.

In a further embodiment, the vessel extends into a transparent vessel isolation chamber, such that the heater element is interposed between the vessel and the vessel isolation chamber and an annular gap adjacent to the heater element is defined between the vessel and the vessel isolation chamber.

In a still further embodiment, the vessel is mounted to a vessel plate. A set of plunger contacts, also mounted to the vessel plate, are connected to the electrical contact element.

According to a further aspect of the present invention, a dissolution testing system comprises a vessel plate, a plurality of vessels mounted to the vessel plate, a plurality of heater elements, and a heater control system. Each vessel includes a lateral wall having an outer surface to which a corresponding heater element is attached. Each heater element includes a transparent surface area, a heat conductive element extending along the transparent surface area, a temperature sensing element extending along the transparent surface area, and an electrical contact element connected to the heat conductive element and the temperature sensing element. The heater control system communicates with each heat conductive element and each temperature sensing element through a corresponding one of the electrical contact elements.

The present invention also provides a method for heating a vessel without the use of a fluid heating medium. A flexible heater element is provided around a circumference of a vessel. The heater element includes a transparent surface area, a heat conductive element extending along the transparent surface area, a temperature sensing element extending along the transparent surface area, and an electrical contact element connected to the heat conductive element and the temperature sensing element. A substance is dispensed into the vessel, and a temperature probe is extended into the substance. Electrical power is supplied to the heat conductive element to cause heat energy to transfer into the substance. Electrical power is also supplied to the temperature sensing element. The temperature probe is used to monitor the temperature of the substance as the substance is heated by the heat conductive element, and to determine when the substance has reached a predetermined set point temperature. A value measured by the temperature sensing element, and which corresponds to the set point temperature, is read. That value is used to maintain the set point temperature.

It is therefore an object of the present invention to provide a vessel heating system that does not rely on a water bath to control and maintain the temperature of a test solution contained in a vessel.

It is another object of the present invention to provide a vessel heating system that is able to independently control individual vessels of a vessel-containing apparatus.

It is a further object of the present invention to provide a vessel heating system that reduces the startup time required for bringing the solution or media contained in one or more vessels to a stabilized, prescribed set point temperature.

Some of the objects of the invention having been stated hereinabove, other objects will become evident as the description proceeds when taken in connection with the accompanying drawings as best described hereinbelow.

BRIEF DESCRIPTION OF THE DRAWINGS

FIG. 11 is a front elevation view of a heater element provided according to another embodiment of the present invention; and FIG. 12 is a vertical cross-sectional view of a heater element according to an another embodiment of the present invention.

DETAILED DESCRIPTION OF THE INVENTION

Figure 1:
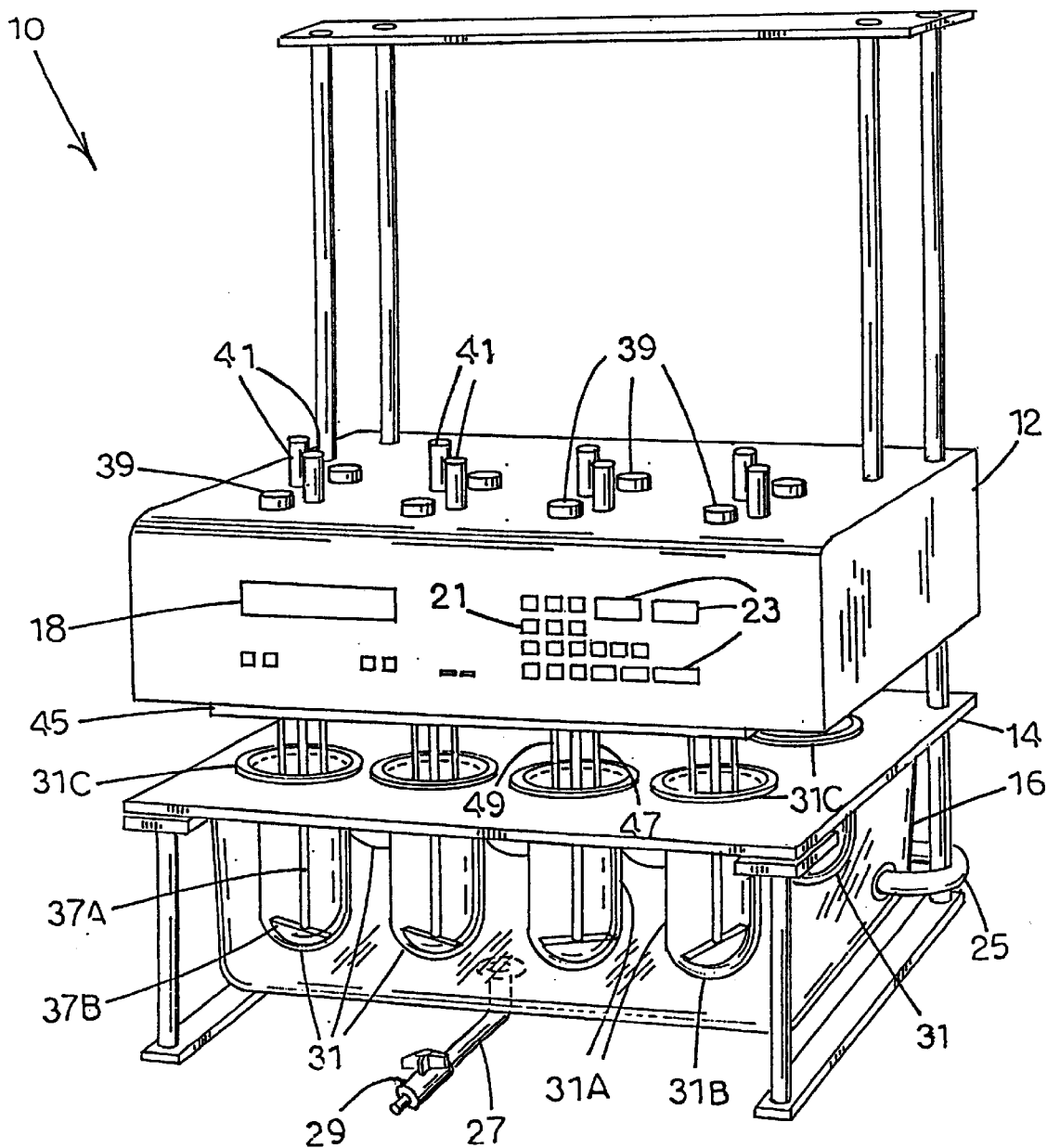
FIG. 1 is a perspective view of a conventional dissolution testing apparatus equipped with a water bath heating system.
Figure 2:
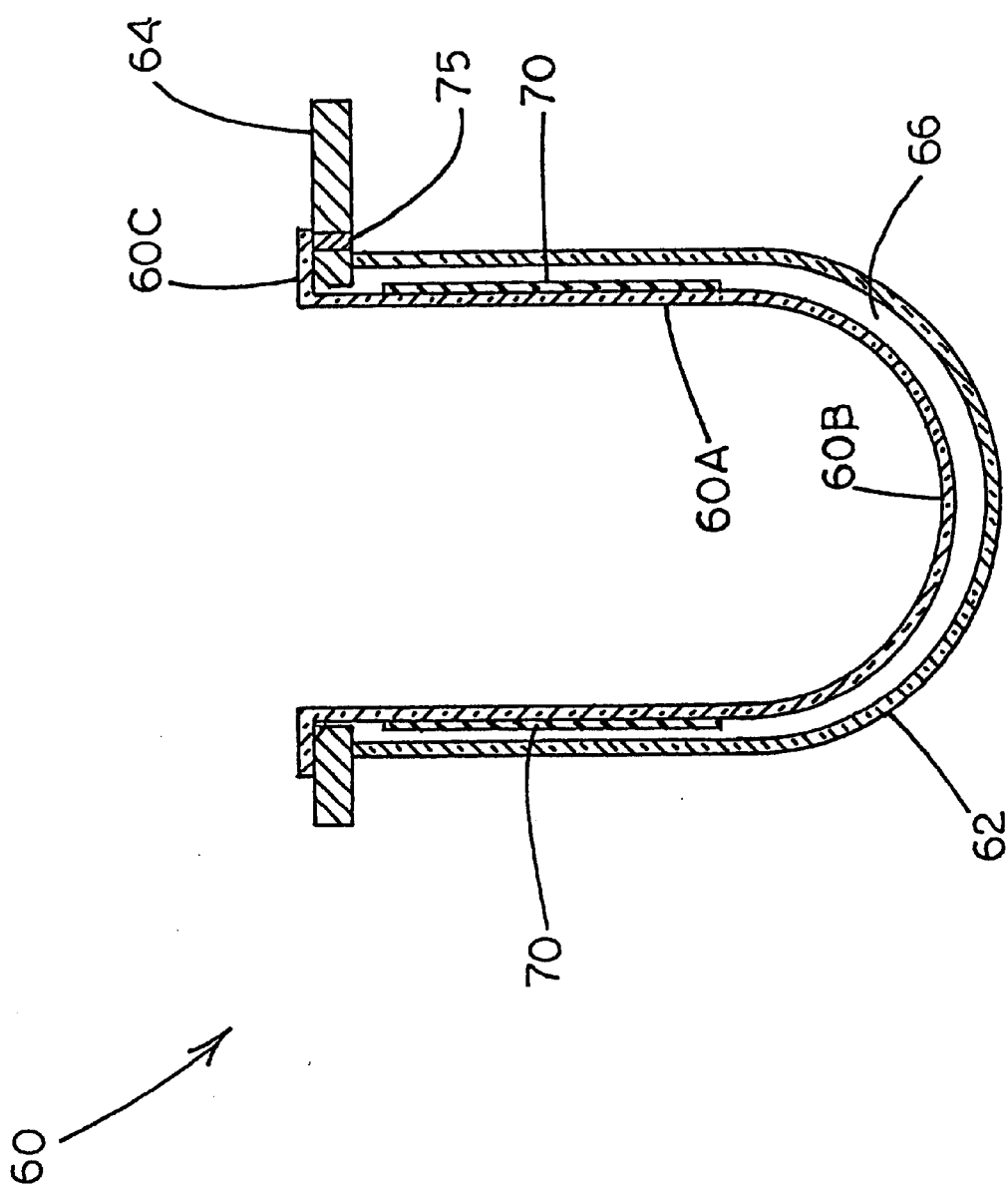
FIG. 2 is a vertical cross-sectional view of a vessel provided according to the present invention.

Referring to FIG. 2, a vessel generally designated 60 is provided as part of a waterless vessel heating system in accordance with the present invention. The design of vessel 60 makes it particularly suited for use in conjunction with many types of dissolution testing apparatuses such as, for example, apparatus 10 shown in FIG. 1. Vessel 60 is a modification of a standard USP vessel having a lateral cylindrical section 60A, a bottom hemispherical section 60B, and a flanged section 60C. A flexible heater element generally designated 70 is attached to the outer surface of cylindrical section 60A. Heater element 70 extends around the entire circumference of cylindrical section 60A. Test data gathered by the inventors have shown that, when vessel 60 is provided with heater element 70 of the present invention, hemispherical section 60B does not need to be heated. This is due in part to the fact that a primary operation of the dissolution testing apparatus is to stir the media contained in vessel 60. This stirring or agitation largely occurs in the interior portion of vessel 60 adjacent to hemispherical section 60B. The rate of heat energy transferred into the vessel media by heater element 70 is sufficiently high that, when combined with the energy added by the stirring element, heat loss from hemispherical section 60B is insignificant.

Additionally, in the present invention a clear plastic or glass vessel isolation chamber wall 62 is mounted to the underside of a modified vessel plate 64. Vessel isolation chamber wall 62 encloses vessel 60 such that an insulating air gap or air barrier 66 is defined between the respective walls of vessel 60 and vessel isolation chamber 62. Test data have shown that air gap 66 has a positive effect in maintaining vessel media temperature and isolating vessel 60 and the media contained therein from external thermal influences.

Figure 3:
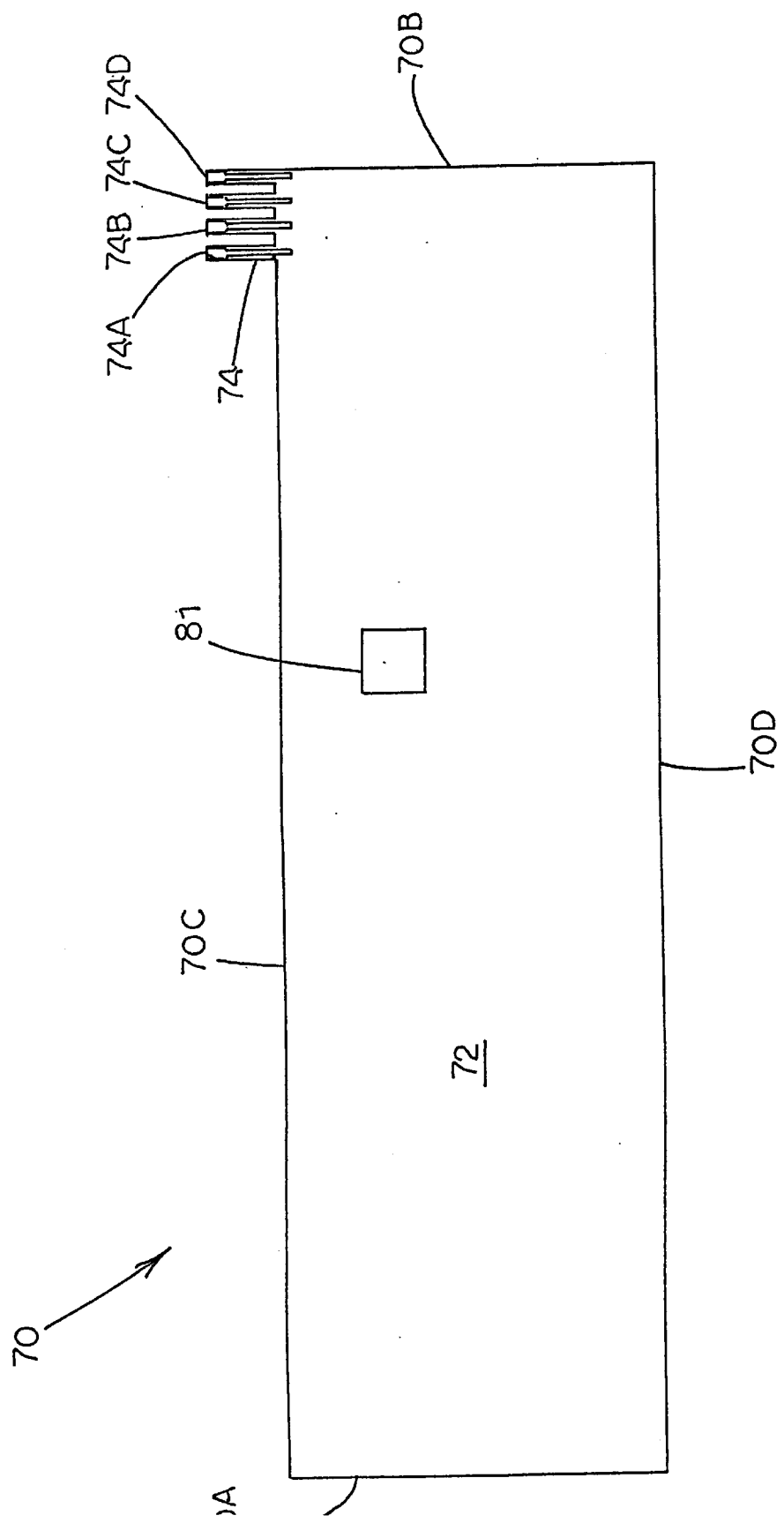
FIG. 3 is a front elevation view of a heater element provided according to the present invention.

Referring to FIG. 3, heater element 70 is shown in uninstalled planar form. Heater element 70 includes a heater area 72 circumscribed by lateral edges 70A and 70B, a top edge 70C, and a bottom edge 70D of heater element 70. Heater element 70 also includes a set of contacts 74 to provide electrical communication between the operative components of heater area 72 and the control system provided with the present invention, to be described below. In this embodiment, contact set 74 includes four electrically conductive contact elements 74A–74D, which can be provided in the form of flat or cylindrical plates or strips. As described below, heater area 72 includes both heat conductive and temperature sensing elements. In addition, heater area includes a protective sensor 81 such as a thermistor, which is embedded within heater area 72 and serves as a preventative device in the event of a control system malfunction.

Figure 4B:
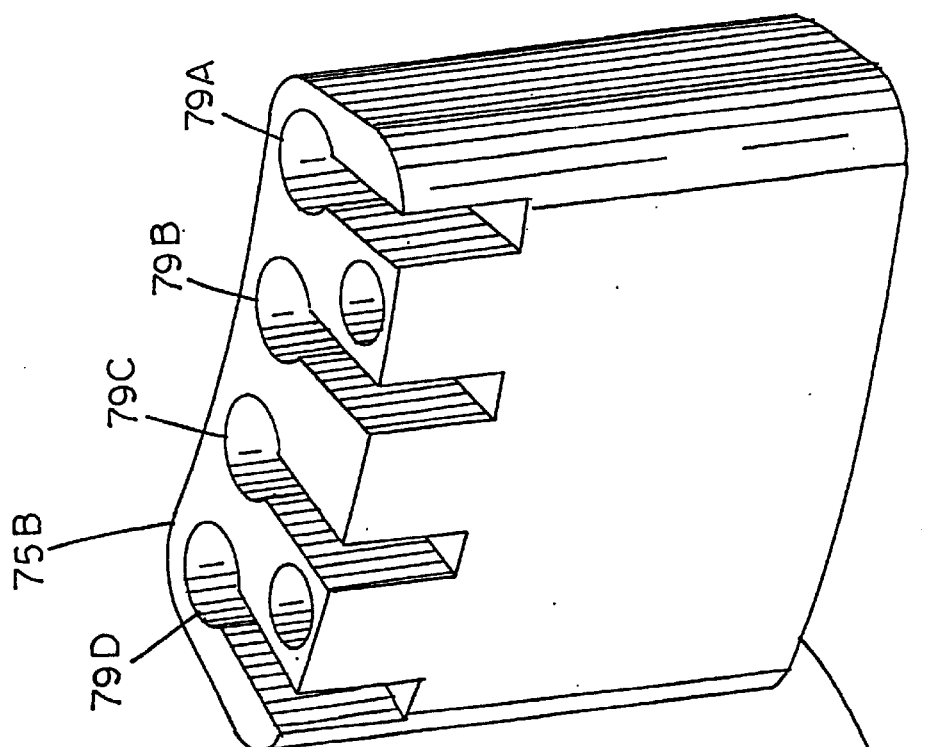
FIG. 4B is another perspective view of the plunger contact element illustrated in FIG. 4A.
Figure 4A:
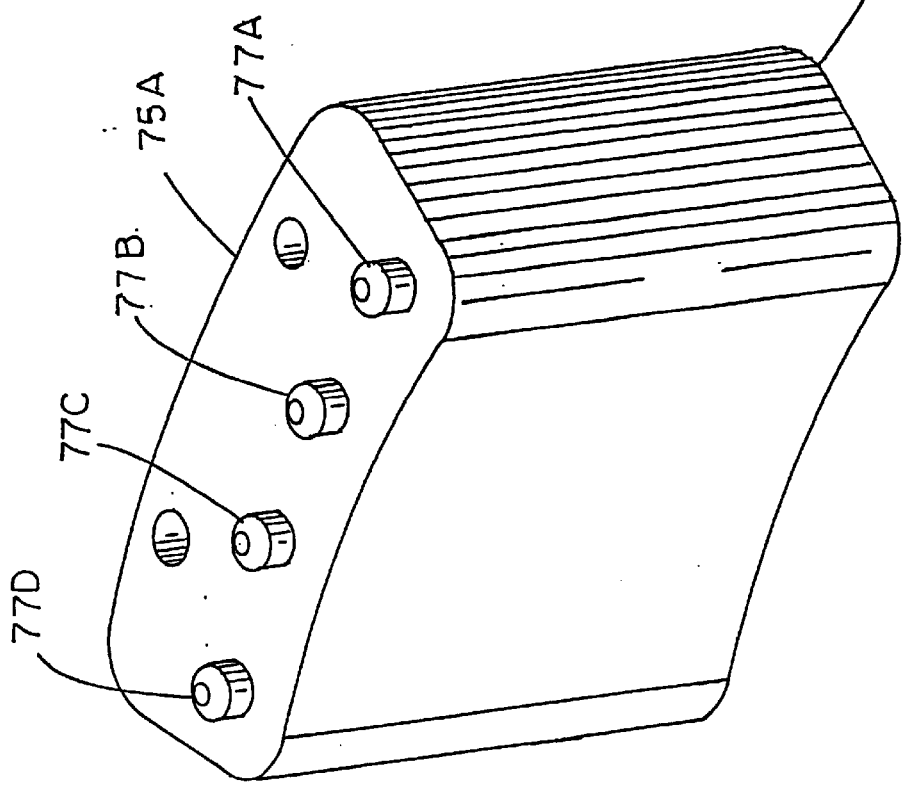
FIG. 4A is a perspective view of a plunger contact element provided in accordance with the present invention.

Referring to FIGS. 4A and 4B, a contact block 75 is utilized to make electrical contact with contact set 74. As shown in FIG. 2, contact block 75 is mounted in vessel plate 64. A set of four stainless steel, gold-plated, spring-loaded plunger contacts 77A–77D protrude from an upper surface 75A of contact block 75. Contact set 74 is preferably situated at the underside of flanged section 60C of vessel 60. Consequently, when vessel 60 is installed in vessel plate 64, contact elements 74A–74D are pressed into contact with corresponding plunger contacts 77A–77D. A lower surface 75B of contact block 75 includes connective features 79A–79D for enabling electrical communication with the control system associated with the present invention.

It can be seen from FIG. 2 that contact block 75 is mounted in a fixed position in vessel plate 64. With respect to the aperture of vessel plate 64 through which vessel 60 is installed, the position of contact block 75 is fixed both radially and circumferentially. As a result, vessel 60 will always be installed in the same location and orientation in vessel plate 64, even after being removed and reinstalled. This is because, in this particular embodiment, installation requires that contact elements 74A–74D of heater element 70 be aligned with plunger contacts 77A–77D of contact block 75. Therefore, the use of contact block 75 enhances the consistency and repeatability of the orientation of vessel 60.

Figure 5:
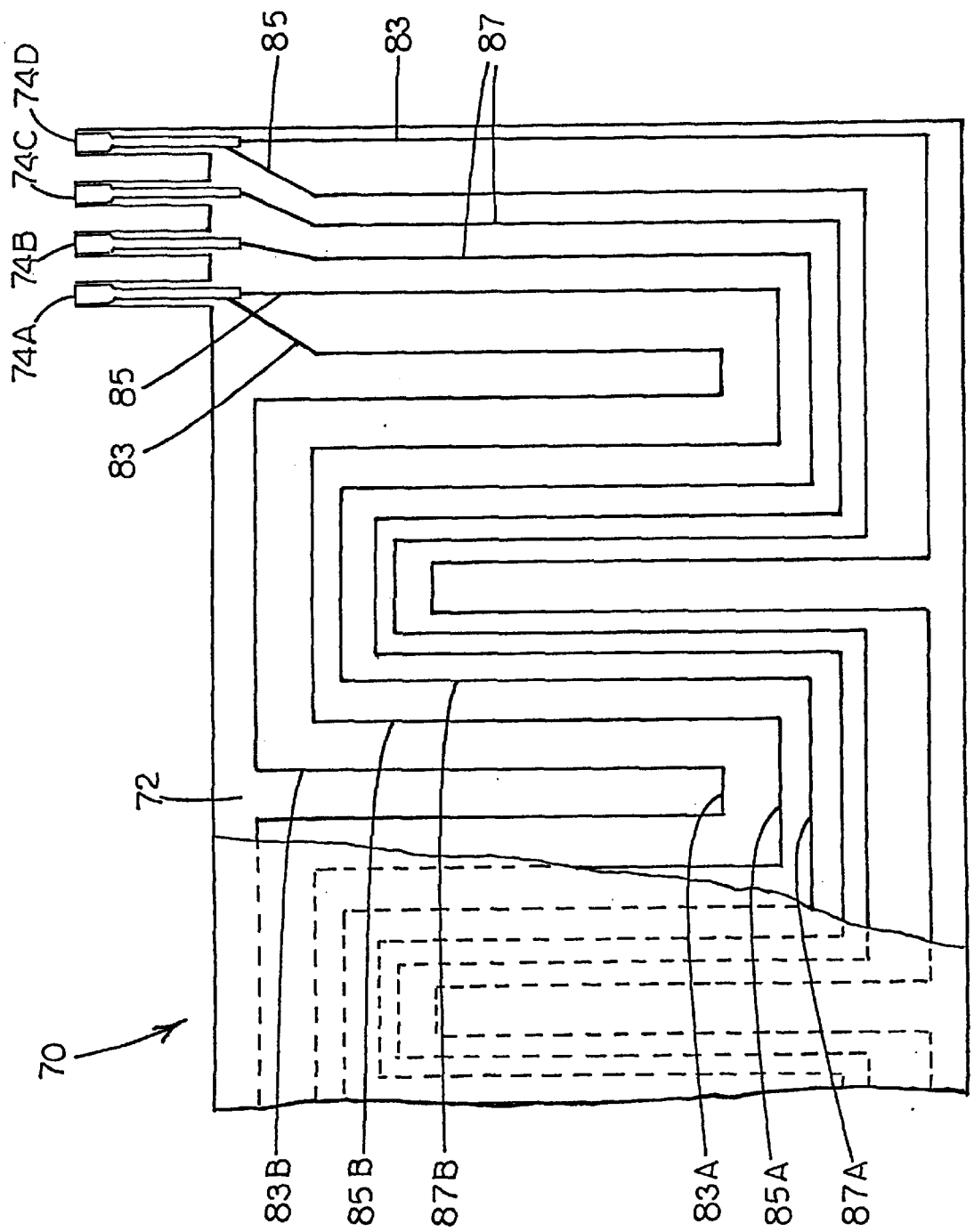
FIG. 5 is a detailed front elevation view of a portion of the heater element illustrated in FIG. 3.

Referring to the detail view of FIG. 5, heat conductive elements 83 and 85 and temperature sensing elements 87 are provided in heater area 72 in the form of a serpentine, alternating wire pattern connected to contact elements 74A–74D and running along substantial portions of the length and height of heater area 72. Accordingly, when heater element 70 is viewed in the planar form illustrated in FIGS. 3 and 5, the course traveled by heat conductive elements 83 and 85 is adjacent to the course traveled by temperature sensing elements 87. Heat conductive elements 83 and 85 are preferably heat conductive wires and temperature sensing element 87 is preferably a temperature sensing wire. Moreover, heat conductive elements 83 and 85 are preferably constructed from a good resistive heat dissipating material such as copper, and temperature sensing element 87 is preferably an RTD in wire form.

Heat conductive elements 83 and 85 each run from first contact element 74A along an alternating course toward lateral edge 70A of heater element 70 (see FIG. 3) and return to fourth contact element 74D to complete the heater circuit. Similarly, temperature sensing element 87 runs from second contact element 74B along an alternating course between heat conductive elements 83 and 85 toward lateral edge 70A, and returns to third contact element 74C to complete the temperature sensing circuit. It can be seen that heat conductive elements 83 and 85 and temperature sensing element 87 each have several respective horizontally oriented sections 83A, 85A and 87A and vertically oriented sections 83B, 85B and 87B. By this design, heat conductive elements 83 and 85 are uniformly distributed over heater area 72 for uniform heat transfer from heater element 70 to the media in vessel 60, and temperature sensing element 87 is uniformly distributed over heater area 72 in order to effectively sense an average temperature of heater element 70 (and thus vessel 60). While FIG. 5 illustrates an embodiment wherein vertically oriented sections 83B, 85B and 87B are the dominant lengths, it will be understood that the wire pattern could be configured such that horizontally oriented sections 83A, 85A and 87A are the dominant lengths. Furthermore, heat conductive elements 83 and 85 and temperature sensing elements 87 could include sections that are angled with respect to the horizontal or the vertical. Such alternative wire patterns can also result in uniform distribution over heater area 72.

Preferably, heat conductive elements 83 and 85 and temperature sensing elements 87 each have continuous lengths throughout heater area 72. However, the number of heat conductive elements 83 and 85 and temperature sensing elements 87, as well as the number of contact elements 74A–74D, are not limited by the present invention to the illustrated embodiments.

In one exemplary embodiment, heater element 70 is 13.1 inches long and 3.875 inches high. The total heater power output delivered is 120 W during operation at a supply voltage of 48 VDC and a current of 3.0 A. Heat conductive elements 83 and 85 have a resistance of 17.6 Ω at 25° C. Temperature sensing element 87 is rated at 1000 Ω averaged over heater area 72. Thermistor 81 is rated at 2.252 kΩ.

Figure 6:
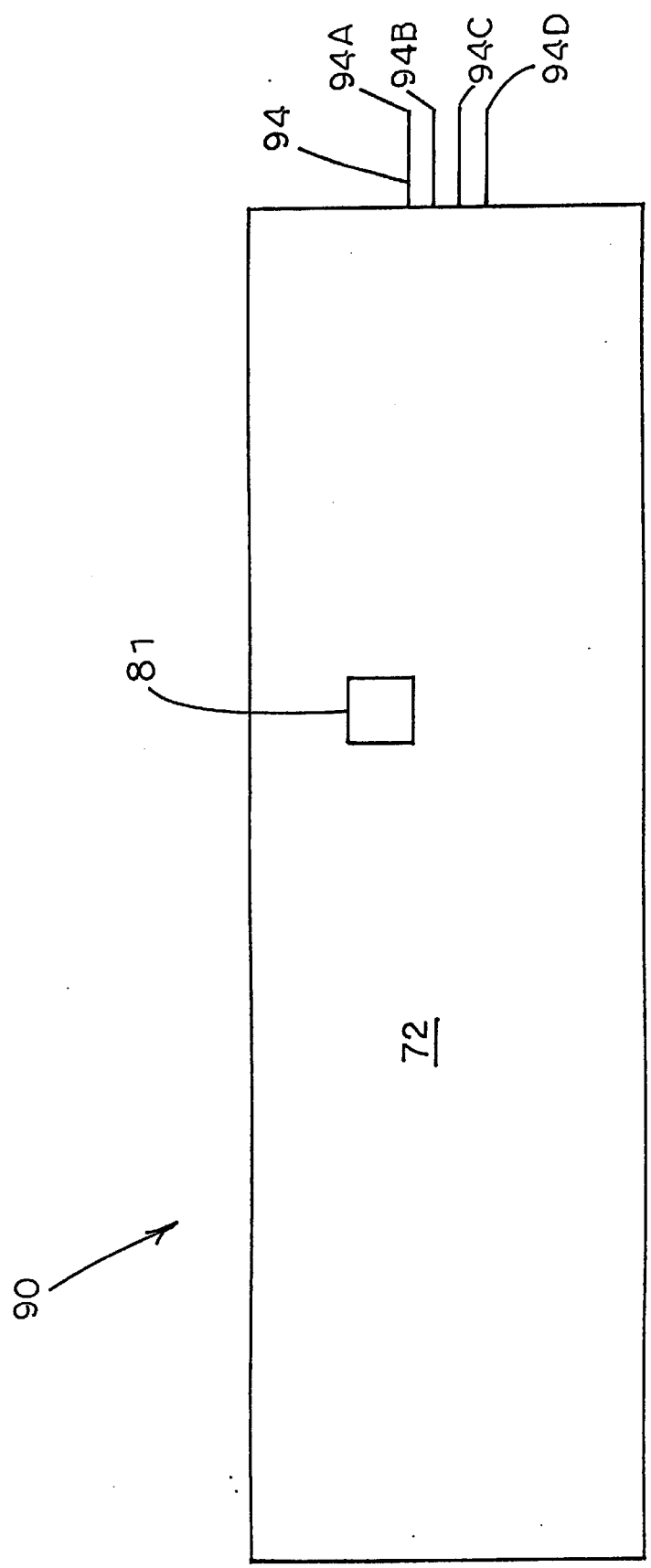
FIG. 6 is a front elevation view of an alternative heater element provided according to the present invention.

Referring to FIG. 6, an alternative heater element generally designated 90 includes a contact set 94 in the form of "pigtails" in which lead wires 94A–94D are substituted for contact elements 74A–74D shown in FIG. 3. The serpentine, alternating wire pattern defined by heat conductive elements 83 and 85 and temperature sensing elements 87 can be designed similar to that shown in FIG. 5.

Heater element 70 (or 90) provided in accordance with the present invention is characterized in that it is flexible and thin. In addition, heater element 70 is highly transparent so as not to impair observation of the vessel media, test substance and the various components operating within vessel 60, such as the stirring element, temperature probe, sample cannula and the like. Accordingly, heater element 70 is constructed as a clear laminate as shown in the cross-sectional views of FIGS. 7 and 8.

Figure 7:
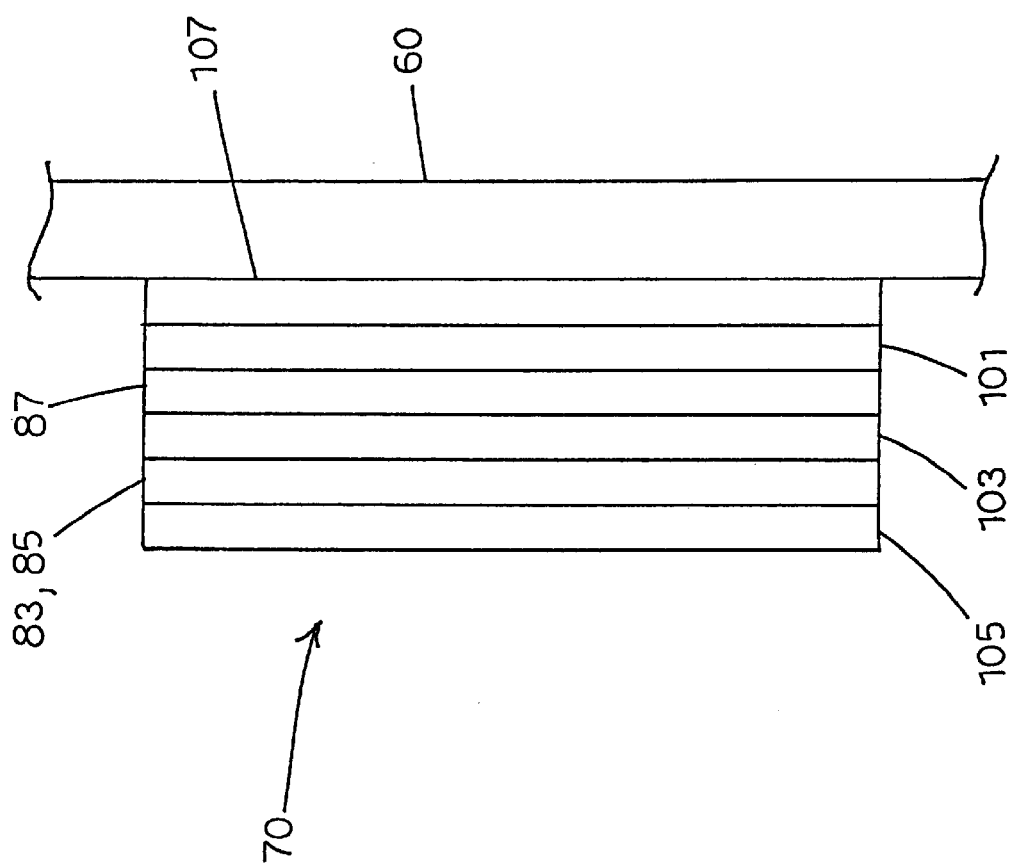
FIG. 7 is a vertical cross-sectional view of a heater element provided according to the present invention.

Referring to FIG. 7, heater element 70 (or 90) is constructed by applying temperature sensing element 87 to a clear polymeric film 101, applying heat conductive elements 83 and 85 to a clear polymeric film 103, and applying an additional clear polymeric film 105 to heat conductive elements 83 and 85. As a result, temperature sensing element 87 is sandwiched between films 101 and 103 and heat conductive elements 83 and 85 are sandwiched between films 103 and 105. The resulting laminate is then secured to the wall of vessel 60 with a suitable pressure-sensitive adhesive 107 such as a high-performance type available from 3M.

Figure 8:
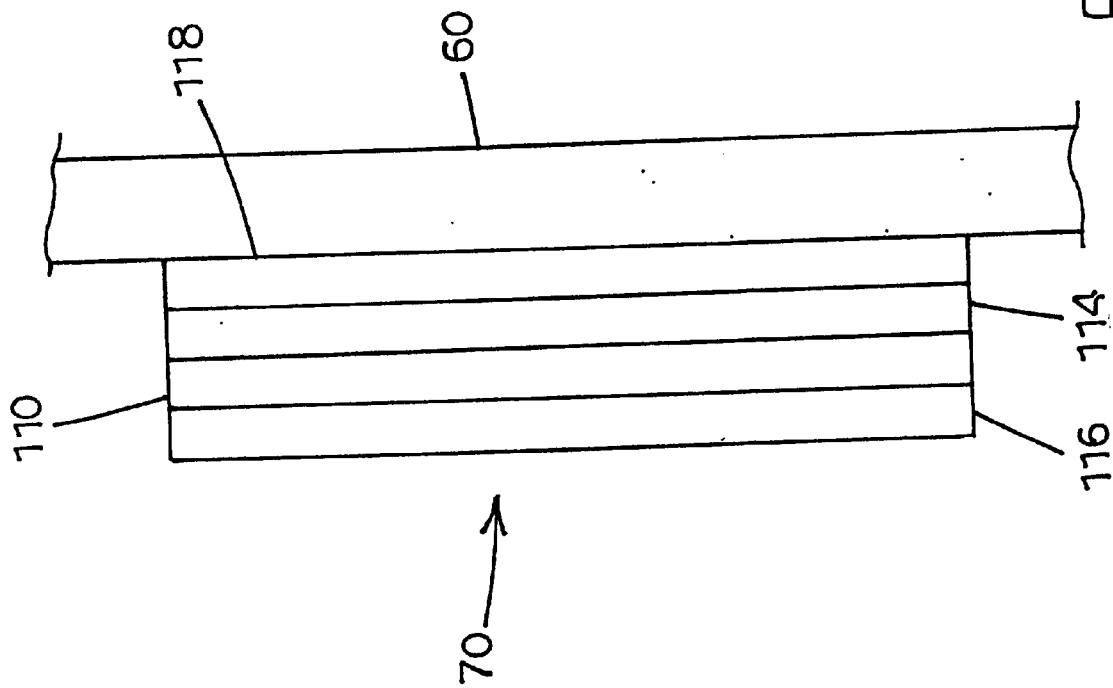
FIG. 8 is a vertical cross-sectional view of an alternative heater element provided according to the present invention.
Figure 8A:
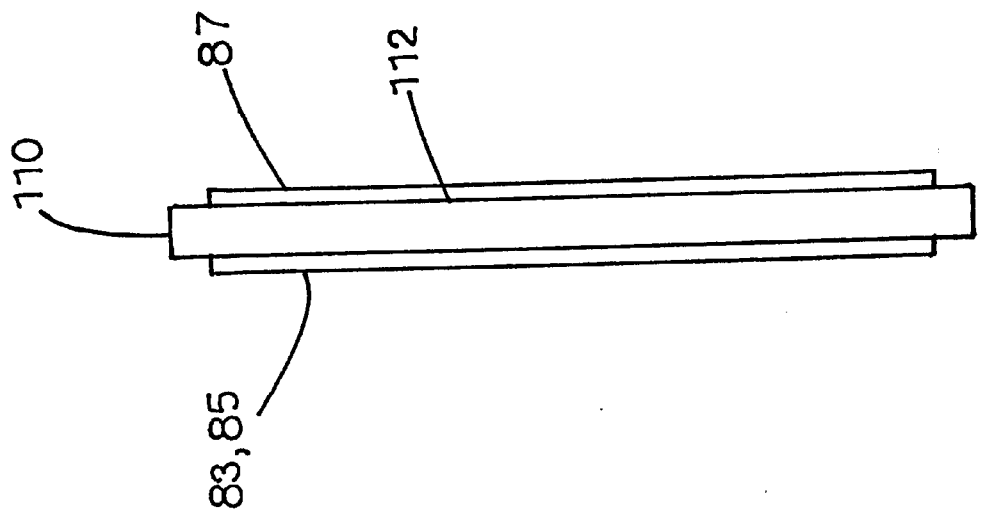
FIG. 8A is a detailed vertical cross-sectional view of an operative portion of the heater element illustrated in FIG. 8.

Referring to FIGS. 8 and 8A, a more preferable construction for heater element 70 (or 90) is illustrated. A composite 110 is sandwiched between two polyester films 114 and 116. As shown in FIG. 8A, the composite 110 is formed by applying temperature sensing element 87 and heat conductive elements 83 and 85 to either side of an internal adhesive 112, such as a high-performance type available from 3M. The resulting laminate is baked directly onto the wall of vessel 60 by employing a polyethylene adhesive 118 such as a high-performance type available from 3M.

Figure 9:
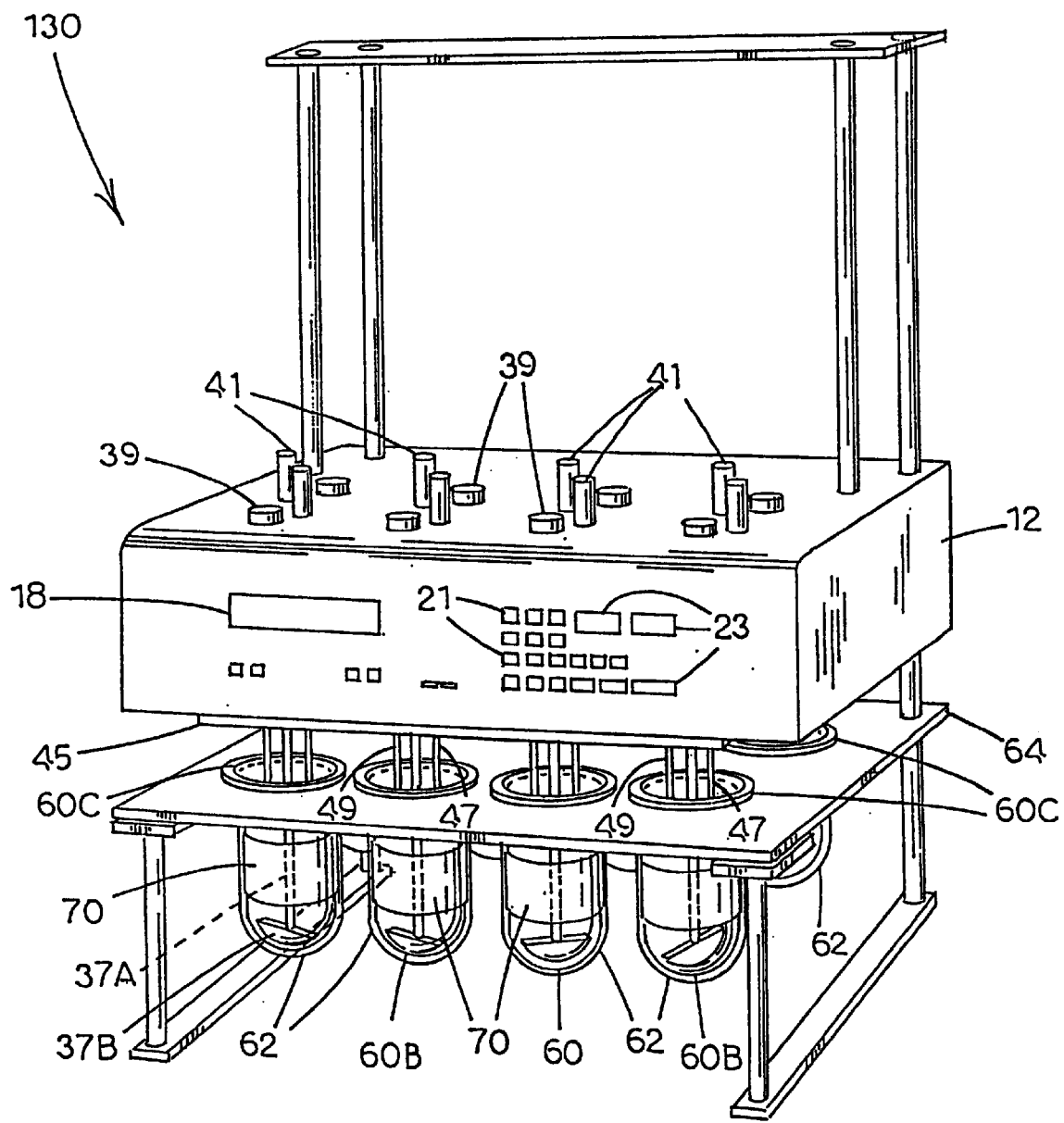
FIG. 9 is a perspective view of a dissolution testing apparatus equipped with a vessel heating system according to the present invention.

Referring to FIG. 9, a dissolution testing apparatus generally designated 130 is provided in accordance with the present invention. A plurality of modified vessels 60 equipped with heater elements 70 (or 90) and vessel isolation chambers 62 are installed in modified vessel plate 64. Sampling manifold 45 preferably is capable of lowering all temperature probes 49 into their respective vessels 60 simultaneously or lowering an individual temperature probe 49 into its vessel 60 apart from other temperature probes 49. With the use of modified vessels 60, the water bath system shown in FIG. 1 is not needed. Other features and components of dissolution testing apparatus 130 can be generally similar to those described in connection with FIG. 1.

Figure 10:
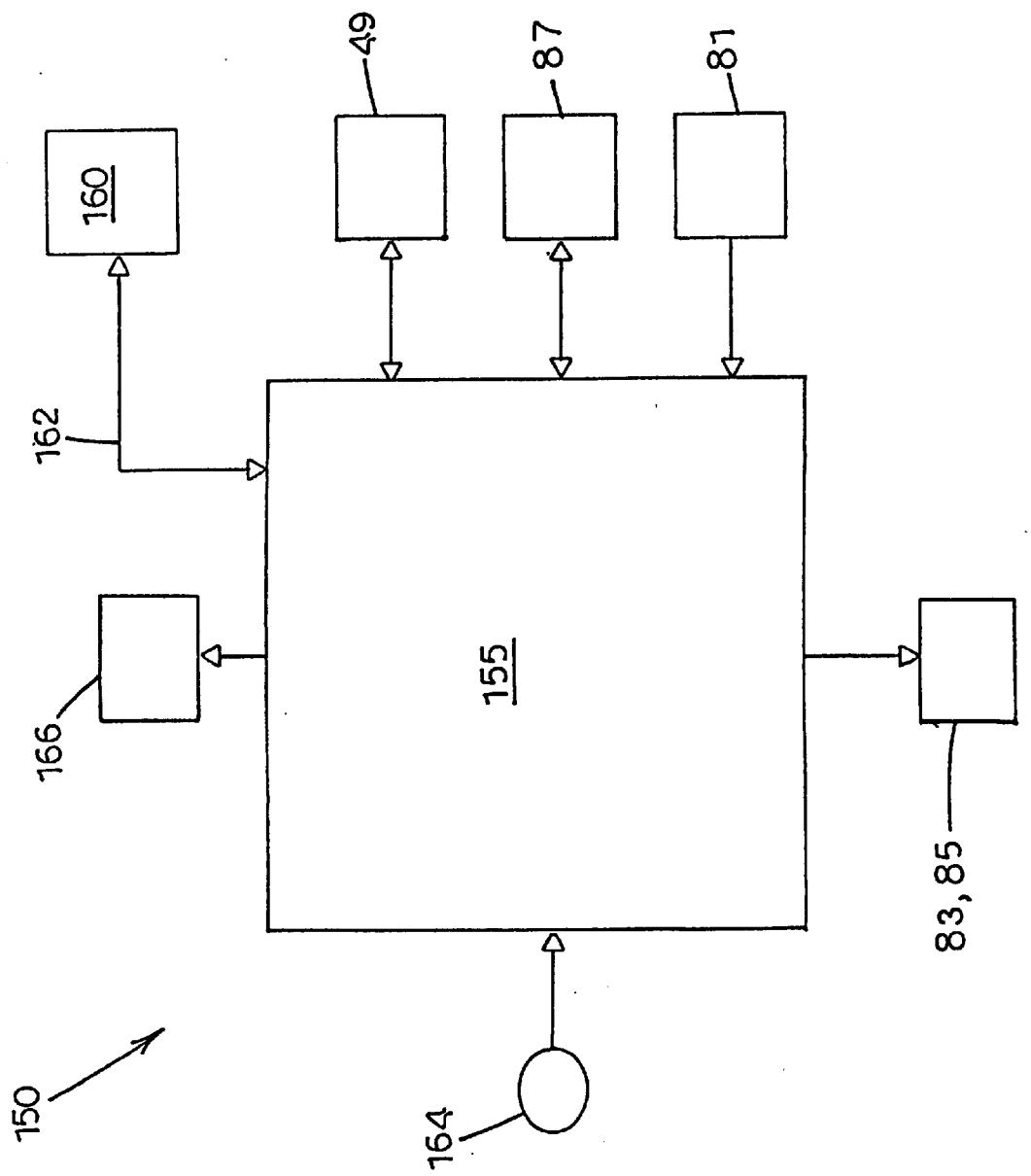
FIG. 10 is a schematic diagram of operative elements included in a vessel heating system according to the present invention.

FIG. 10 is a general schematic diagram of a waterless vessel heating control system generally designated 150 provided in accordance with the present invention to operate in conjunction with an apparatus such as dissolution testing apparatus 130 equipped with one or more vessels 60. Heating system control circuitry or controller 155 is adapted to communicate with main control circuitry 160 of dissolution testing apparatus 130 over a dedicated communication link 162, and hence can be housed within main head 12 of such apparatus 130. Preferably, controller 155 operates according to a set of instructions provided by system software, and therefore controller 155 and/or main control circuitry 160 include appropriate memory, logic and interface components as understood by those skilled in the art. Controller 155 independently operates heat conductive elements 83 and 85 of each vessel 60 by controlling the power supplied thereto. Controller 155 also powers and receives signals from temperature sensing element 87 as well as protective sensor 81 provided with each heater element 70. Controller 155 further communicates with each temperature probe 49 associated with each vessel 60. Element 164 represents means such as a keypad for enabling user input of vessel media set point temperature and other appropriate system parameters for each vessel 60. Element 166 represents a device for displaying temperature and other information pertinent to the vessel heating process.

It therefore can be seen that control system 150 is able to simultaneously and individually control and maintain each vessel 60 at a given temperature, with an observed accuracy of ±0.1° C., and permits each vessel 60 to be set at a different temperature if desired. Moreover, control system 150 is configured to minimize initial startup time of each heated vessel 60. For instance, the startup time required to bring the media in a 900-mL vessel from room temperature to a stabilized set point temperature of about 37 or 38° C. has been observed to be approximately less than 9 minutes, which represents a significant improvement over water bath systems. Control system 150 is further characterized by its use of three temperature sensors per vessel 60. Specifically, temperature probe 49 is used for monitoring of startup conditions and instantaneous monitoring of vessel media temperature after stabilization. Temperature sensing element 87 is used for controlling heater element/vessel temperature and thus ultimately controlling vessel media temperature. Protective sensor 81 is preferably a thermistor used as a safety measure to prevent heater element 70 from self-destructing in the event of a malfunction.

Referring now to FIG. 11, a heater element generally designated 170 is shown in uninstalled planar form according to another embodiment of the invention. In this embodiment, heater element 170 includes a plurality of heater zones or areas 172A and 172B circumscribed by lateral edges 170A and 170B, a top edge 170C, and a bottom edge 170D of heater element 170. In the specific embodiment illustrated in FIG. 11, heater element 170 includes an upper heater area 172A and a lower heater area 172B so as to be in thermal contact with upper and lower portions of a vessel 60, respectively. Contact set 174 includes at least one additional contact element, when compared to the embodiment illustrated in FIG. 3. Thus, for example, contact set 174 in FIG. 11 includes five electrically conductive contact elements 174A–174E, which can be provided in the form of flat or cylindrical plates or strips (or with profiles having both flat and cylindrical elements). One of contact elements 174A–174E serves as a common connection between upper heater area 172A and a lower heater area 172B and thus serves as a center tap. At least one other contact element 174A–174E is connected to upper heater area 172A, and at least one other contact element 174A–174E is connected to lower heater area 172B. With the use of the center tap and thus the localized, common connection between upper heater area 172A and lower heater area 172B, heater element 170 of FIG. 11 remains essentially a single heating device but with two distinct heating zones. If used in conjunction with heater element 170 of FIG. 11, contact block 75 illustrated in FIGS. 4A and 4B is modified to include the appropriate number of plunger contacts necessary for connection with contact elements 174A–174E.

With analogous reference to FIG. 5, the heat conductive elements provided in both upper heater area 172A and lower heater area 172B are preferably one or more wires that run along serpentine courses to cover a substantial portion of upper and lower heater areas 172A and 172B, respectively. In the present configuration, one of the heat conductive elements runs between upper and lower heater areas 172A and 172B through that contact element 174A–174E serving as the center tap. By this configuration, the energization of one or both of heater areas 172A and 172B can be easily and quickly controlled. For example, if a vessel 60 contains 900 mL of dissolution media, contact set 174 will be energized so that electrical current runs through the heat conductive elements of both upper and lower heater areas 172A and 172B. If, on the other hand, vessel 60 contains 500 mL of dissolution media, contact set 174 will be energized so that electrical current runs through the heat conductive element or elements of only lower heater area 172B.

Heater element 170 of FIG. 11 also includes temperature sensing elements, such as temperature sensing elements 87 shown in FIG. 5, which are preferably in the form of an RTD connected to two of contact elements 174A–174E. This temperature sensing element (or elements) runs along a temperature sensing area 185 that is situated within lower heater area 172B in the sense of being radially adjacent thereto, since lower heater area 172B operates regardless of the volume of dissolution media in vessel 60 to be heated. In addition, heater element 170 can include one or more protective sensors, such as shown in FIG. 5, which is embedded within either or both of upper and lower heater areas 172A and 172B. It will be further noted that heater element 170 can operate in connection with dissolution test apparatus 130 illustrated in FIG. 9. Additionally, control system 150 described hereinabove with reference to FIG. 10 can be programmed through user input to select whether one or both of heater areas 172A and 172B is to be operational during use of the invention, such as by allowing the user to specify the volume of the contents of the vessel or vessels 60 to be heated.

In one example corresponding to the embodiment illustrated in FIG. 11, heater element 170 is 13.0 inches long and 3.0 inches high. The total heater power output delivered is 160 W. Heater element 170 could be configured, for example, such that 80 W of power are delivered to upper heater area 172A and 80 W delivered to lower heater area 172B.

Referring to FIG. 12, a suitable construction of heater element 170 is illustrated. This construction comprises a polymeric (e.g., polyester) film 181; an adhesive layer or application 183; a layer 184 representing the heat conductive and temperature sensing elements respectively disposed in upper heating area 172A, lower heating area 172B, and temperature sensing area 185 (see FIG. 11); another polymeric film 187 disposed on the other side of layer 185; and another adhesive layer or application 189. The resulting laminate is attached to the wall of vessel 60. The construction illustrated in FIG. 12 could also serve as an alternative to the constructions illustrated in FIGS. 7, 8 and 8A for heater elements 70 and 90. Likewise, heater element 170 could be implemented in the constructions shown in FIGS. 7, 8 and 8A.

In operation, and using heater elements 70, 90 or 170 according to any of the embodiments described herein, the software of control system 150 upon startup initiates a vessel self-test routine, which checks each vessel 60 for proper electrical contact and installation in vessel plate 64. Preferably, this is accomplished by applying a voltage to each heater element 83 and 85 for a very short time and measuring the voltage drop across an in-line resistor. After the vessel self-test routine is completed, the status of each vessel 60 is displayed (e.g., "OK" or "FAIL"). This vessel self-test routine is preferably accessible at any time by the user of dissolution testing apparatus 130 for on-the-fly diagnostic purposes. In order to afford the user the option of setting different operating temperatures for each vessel 60 or each group of vessels 60, the software preferably prompts the user to either "SET ALL" or "SET INDIVIDUAL" vessel temperatures. If the SET ALL option is selected, the user will be prompted to enter the value for a single set point temperature, and that value will be utilized by controller 155 to control all vessels 60 installed on vessel plate 64. If the SET INDIVIDUAL option is selected, the user will be prompted to enter a set point temperature value for each individual vessel 60 operating in apparatus 130.

When the vessel heating system is then turned ON, controller 155 conducts an appropriate amount of power to heat conductive elements 83 and 85 of each heater element 70 in accordance with the set point value entered for corresponding vessel 60. Head 12 of dissolution testing apparatus 130 moves down toward vessel plate 64 and sampling manifold 45 lowers each temperature probe 49 down into the media of each vessel 60. At this stage, controller 155 utilizes each temperature probe 49 as the primary sensor and initial source for control of vessel 60 into which respective temperature probe 49 is lowered. Temperature probes 49 send signals to controller 155 indicative of the media temperatures measured in respective vessels 60, such that controller 155 monitors the rise in media temperature in each vessel 60.

Controller 155 determines that the media temperature in a given vessel 60 has stabilized at the previously inputted set point based on an appropriate condition written into the software. Preferably, controller 155 determines the occurrence of stabilization when controller 155 reads a series of media temperature values from a given temperature probe 49 that deviate less than ±0.05° C. from the set point value previously established for that vessel 60 over a 10 second period.

Once controller 155 determines that the media temperature in a particular vessel 60 has stabilized at the programmed set point value, controller 155 in effect passes the sensory function from temperature probe 49 associated with that vessel 60 over to temperature sensing element 87 of heater element 70 corresponding to that vessel 60. The temperature value read by temperature sensing element 87 can be characterized as the vessel or heater element temperature and will be somewhat higher than, but nevertheless directly proportional to, the actual temperature value of the media contained in vessel 60. For example, if the set point value of the media is 37° C., the value measured by temperature sensing element 87 might be 39° C. At this point, controller 155 locks in the value measured by temperature sensing element 87, associates that value with the level of power to be distributed to corresponding heat conductive elements 83 and 85 of heater element 70, and utilizes temperature sensing element 87 as the primary control sensor. After all vessels 60 are stabilized at their respective set point temperatures and control has been switched to temperature sensing elements 87, sampling manifold 45 is moved upwardly to remove temperature probes 49 from vessels 60 and a message is displayed indicating that all vessels 60 have reached their set point temperatures.

The value measured by each temperature sensing element 87 is then utilized by controller 155 during the media sampling process to control the media temperature for that particular vessel 60. During media sampling, temperature probes 49 can be periodically employed to measure and verify the actual media temperatures. If the media temperature of a given vessel 60 is determined to be outside an appropriate error tolerance (e.g., ±0.05° C.), controller 155 makes the adjustment to the temperature sensing element value necessary to bring the media temperature back within the prescribed limits. Protective sensor 81, upon detecting a malfunction such as a runaway temperature condition, will send a signal to controller 155 to shut the system down.

It will be understood that the present invention is not limited to the specific context of dissolution testing equipment, but rather finds utility in any apparatus or procedure wherein the contents of a vessel or vessels are to undergo a controlled temperature profile.

It will be further understood that various details of the invention may be changed without departing from the scope of the invention. Furthermore, the foregoing description is for the purpose of illustration only, and not for the purpose of limitation—the invention being defined by the claims. It will be understood that various details of the invention may be changed without departing from the scope of the invention. Furthermore, the foregoing description is for the purpose of illustration only, and not for the purpose of limitation—the invention being defined by the claims.

What is claimed is:

1. A heater element comprising:
   (a) a plurality of clear, flexible films;
   (b) a heat conductive element interposed between the films and comprising a first elongate heat conductive portion and a second elongate heat conductive portion, the first portion extending over a first surface area of the heater element along a first alternating, serpentine course, and the second portion extending over a second surface area of the heater element along a second alternating, serpentine course;
   (c) a temperature sensing element interposed between the films and including an elongate temperature sensing portion extending over a third surface area of the heater element along a third alternating, serpentine course adjacent to the second course; and (d) an electrical contact element connected to the heat conductive element and the temperature sensing element.

2. The heater element according to claim 1 wherein the heat conductive element includes an electrically resistive material adapted to dissipate heat in response to an electrical current flowing therethrough.

3. The heater element according to claim 1 wherein each of the first and second elongate heat conductive portions includes a plurality of horizontal and vertical portions substantially uniformly distributed over its corresponding surface area of the heater element.

4. The heater element according to claim 1 wherein the temperature sensing element is a resistive thermal device.

5. The heater element according to claim 1 wherein the elongate temperature sensing portion includes a plurality of horizontal and vertical portions substantially uniformly distributed over the third surface area of the heater element.

6. The heater element according to claim 1 wherein the third surface area is disposed within the second surface area.

7. The heater element according to claim 1 wherein the electrical contact element includes a first contact plate connected to the first elongate heat conductive portion of the heat conductive element, a second contact plate connected to the second elongate heat conductive portion, and a third contact plate connected to a first portion of the temperature sensing element.

8. The heater element according to claim 7 wherein the electrical contact element includes a fourth contact plate connected to a second portion of the temperature sensing element.

9. The heater element according to claim 8 wherein the electrical contact element includes a fifth contact plate interconnecting the first and second elongate heat conductive portions of the heat conductive element.

10. The heater element according to claim 1 wherein the electrical contact element includes a contact plate interconnecting the first and second elongate heat conductive portions of the heat conductive element.

11. The heater element according to claim 1 comprising a protective sensor attached to at least one the surface areas of the heater element.

12. The heater element according to claim 11 wherein the protective sensor includes a thermistor.

13. The heater element according to claim 1 wherein the plurality of films includes a first film and a second film, the temperature sensing element is interposed between the first and second films and adhered to a first side of an internal adhesive, and the heat conductive element is interposed between the first and second films and adhered to a second side of the internal adhesive.

14. The heater element according to claim 1 wherein the plurality of films includes a first film, a second film and a third film, the temperature sensing element is interposed between the first and second films, and the heat conductive element is interposed between the second and third films.

15. The heater element according to claim 1 wherein the plurality of films includes a first film and a second film, and the temperature sensing and heat conductive elements are interposed between the first film and the second film.

16. A heater element for mounting to a wall of a vessel, the heater element comprising:

(a) first and second clear, flexible films;
(b) a temperature sensing element interposed between the first and second films and adhered to a first side of an internal adhesive;
(c) a heat conductive element interposed between the first and second films and adhered to a second side of the internal adhesive, the heat conductive element comprising a first heat conductive portion disposed in a first heating zone and a second heat conductive portion disposed in a second heating zone adapted for location adjacent to a lower portion of a vessel relative to the first heating zone, wherein the temperature sensing element is disposed in the second heating zone; and
(d) an electrical contact element connected to the heat conductive element and the temperature sensing element.

17. The heater element according to claim 16 wherein the electrical contact element includes a common contact interconnecting the first and second heat conductive portions of the heat conductive element.

18. The heater element according to claim 16 wherein the temperature sensing portion extends through the second heating zone generally along a serpentine course.

19. The heater element according to claim 16 wherein the first heat conductive portion extends through the first heating zone generally along a first serpentine course, and/or the second heat conductive portion extends through the second heating zone generally along a second serpentine course.

20. A heater element for mounting to a wall of a vessel, the heater element comprising:

(a) first, second, and third clear, flexible films;
(b) a temperature sensing element interposed between the first and second films;
(c) a heat conductive element interposed between the second and third films, the heat conductive element comprising a first heat conductive portion disposed in a first heating zone and a second heat conductive portion disposed in a second heating zone adapted for location adjacent to a lower portion of a vessel relative to the first heating zone, wherein the temperature sensing element is disposed in the second heating zone; and
(d) an electrical contact element connected to the heat conductive element and the temperature sensing element.

21. The heater element according to claim 20 wherein the electrical contact element includes a common contact interconnecting the first and second heat conductive portions of the heat conductive element.

22. The heater element according to claim 20 wherein the temperature sensing portion extends through the second heating zone generally along a serpentine course.

23. A heater element for mounting to a wall of a vessel, the heater element comprising:

(a) a plurality of clear, flexible films;
(b) a temperature sensing element interposed between the films and including an elongate temperature sensing portion, the elongate temperature sensing portion extending over a surface area of the heater element and defining an embedded wire pattern;
(c) a heat conductive element interposed between the films and extending throughout a first heating zone and a second heating zone adapted for location adjacent to a lower portion of a vessel relative to the first heating zone, wherein the temperature sensing element is disposed in the second heating zone; and
(d) an electrical contact element connected to the heat conductive element and the temperature sensing element.

24. The heater element according to claim 23, wherein the heat conductive element includes a first elongate heat conductive portion extending throughout the first heating zone and a second elongate heat conductive element extending throughout the second heating zone, and the temperature sensing element and the heat conductive element cooperatively define the embedded wire pattern.

25. The heater element according to claim 23 wherein the electrical contact element includes a common contact interconnecting the first and second heat conductive portions of the heat conductive element.

26. The heater element according to claim 23 wherein at least a portion of the heat conductive element extends through the second heating zone generally along a serpentine course.

27. A vessel heating system comprising:
(a) a vessel including a lateral wall having an outer surface; and
(b) a flexible, substantially transparent heater element attached to the outer surface of the lateral wall, the heater element comprising a first heating zone and a second heating zone, a first heat conductive element disposed in the first heating zone, a second heat conductive element disposed in the second heating zone, a temperature sensing element disposed in at least one of the heating zones, and an electrical contact element connected to the first heat conductive element, the second heat conductive element, and the temperature sensing element.

28. The vessel heating system according to claim 27 wherein the first heating zone is disposed above the second heating zone in relation to the lateral wall, and the temperature sensing element is disposed in the second heating zone.

29. The vessel heating system according to claim 27 comprising a common electrical contact interconnecting the first and second heat conductive elements.

30. The vessel heating system according to claim 27 comprising a transparent chamber wall defining a vessel isolation chamber, wherein the vessel extends into the vessel isolation chamber, the heater element is interposed between the vessel and the chamber wall, and the vessel and chamber wall cooperatively define an annular gap adjacent to the heater element.

31. The vessel heating system according to claim 27 wherein the vessel is mounted to a vessel plate.

32. The vessel heating system according to claim 31 comprising a set of plunger contacts mounted to the vessel plate and connected to the electrical contact element.

33. The vessel heating system according to claim 31 comprising a transparent chamber wall defining a vessel isolation chamber, wherein the vessel extends into the vessel isolation chamber, the heater element is interposed between the vessel and the chamber wall, and the vessel and chamber wall cooperatively define an annular gap adjacent to the heater element.

34. The vessel heating system according to claim 27 comprising a temperature probe extendable into an interior space of the vessel.

35. The vessel heating system according to claim 27 comprising a heater control circuit communicating with the first and second heat conductive elements and the temperature sensing element through the electrical contact element.

36. The vessel heating system according to claim 35 comprising a temperature probe extendable into an interior space of the vessel and communicating with the heater control circuit.

37. The vessel heating system according to claim 36 comprising a protective sensor attached to the heater element and communicating with the heater control circuit.

38. The vessel heating system according to claim 35 comprising a plurality of vessels and a plurality of corresponding heater elements, wherein the heater control circuit communicates with the first and second heat conductive elements of each heater element and with the temperature sensing element of each heater element.

39. The vessel heating system according to claim 27 wherein the flexible heater element is attached to the outer surface of the lateral wall of the vessel by a pressure-sensitive adhesive.

40. The vessel heating system according to claim 27 wherein the flexible heater element is baked onto the outer surface of the lateral wall of the vessel.

41. The vessel heating system according to claim 27 comprising means for mounting the vessel in a consistent, repeatable position with respect to a vessel plate.

42. A dissolution testing system comprising:
(a) a vessel plate;
(b) a plurality of vessels mounted on the vessel plate, each vessel including a lateral wall having an outer surface;
(c) a plurality of flexible, substantially transparent heater elements, each heater element attached to the outer surface of the lateral wall of a corresponding one of the vessels, wherein each heater element comprises a first heating zone and a second heating zone, a first heat conductive element disposed in the first heating zone, a second heat conductive element disposed in the second heating zone, a temperature sensing element disposed in at least one of the heating zones, and an electrical contact element connected to the first heat conductive element, the second heat conductive element, and the temperature sensing element; and
(d) a heater control system communicating with each heat conductive element and each temperature sensing element through a corresponding one of the electrical contact elements.

43. The dissolution testing system according to claim 42 wherein, for at least one of the heater elements, the first heating zone is disposed above the second heating zone in relation to the lateral wall, and the temperature sensing element is disposed in the second heating zone.

44. The dissolution testing system according to claim 42 wherein at least one of the heater elements comprises a common electrical contact interconnecting the first and second heat conductive elements.

45. The dissolution testing system according to claim 42 comprising a plurality of transparent chamber walls defining respective vessel isolation chambers and mounted to the vessel plate, wherein each vessel extends into a corresponding one of the vessel isolation chambers, each heater element is interposed between its corresponding vessel and chamber wall, and each corresponding vessel and chamber wall cooperatively define an annular gap adjacent to the heater element.

46. The dissolution testing system according to claim 42 comprising a plurality of temperature probes, each temperature probe extendable into a corresponding one of the vessels and communicating with the heater control system.

47. The vessel heating system according to claim 42 comprising means for mounting each vessel respectively in a consistent, repeatable position with respect to a vessel plate.

48. A method for heating a vessel without the use of a fluid heating medium comprising the steps of:
(a) providing a flexible, substantially transparent heater element around a circumference of a vessel, the heater element including a first heating zone and a second heating zone, a first heat conductive element disposed in the first heating zone, a second heat conductive element disposed in the second heating zone, a temperature sensing element disposed in at least one of the heating zones, and an electrical contact element connected to the first heat conductive element, to the second heat conductive element, and the temperature sensing element;

(b) dispensing an amount of a substance into the vessel;

(c) extending a temperature probe into the substance;

(d) supplying electrical power to one or both of the heating zones, depending on the amount of substance dispensed into the vessel, to cause heat energy to transfer into the substance by energizing;

(e) supplying electrical power to the temperature sensing element;

(f) using the temperature probe to monitor the temperature of the substance as the substance is heated by the heat conductive element, and to determine when the substance has reached a predetermined set point temperature;

(g) reading a value measured by the temperature sensing element corresponding to the set point temperature; and (h) using the value measured by the temperature sensing element to maintain the set point temperature.

49. The method according to claim 48 comprising the step of extending the vessel into a vessel isolation chamber to reduce the effects of external thermal influences.

50. The method according to claim 48 comprising the steps of providing a vessel plate, mounting a contact block to the vessel plate, and connecting the electrical contact element to the contact block to ensure that the vessel is disposed in a consistent, repeatable position with respect to the vessel plate.

* * * * *